United States Patent [19]
Iwanaga et al.

[11] Patent Number: 5,861,378
[45] Date of Patent: Jan. 19, 1999

[54] HORSESHOE CRAB HEMOCYTE POLYPEPTIDES, AND PREPARATION AND DNA ENCODING THEREOF

[75] Inventors: Sadaaki Iwanaga; Shun-ichiro Kawabata; Tetsu Saito, all of Fukuoka, Japan

[73] Assignee: Seikagaku Kogyo Kabushiki Kaisha (Seikagaku Corp.), Tokyo, Japan

[21] Appl. No.: 505,617

[22] Filed: Jul. 21, 1995

[30] Foreign Application Priority Data

Jul. 22, 1994 [JP] Japan ..................................... 6-191850
Sep. 1, 1994 [JP] Japan ..................................... 6-232025

[51] Int. Cl.$^6$ ......................... A61K 38/17; C07K 14/435
[52] U.S. Cl. ................................ 514/12; 514/2; 530/324; 530/357; 530/300
[58] Field of Search ........................... 930/361; 530/300, 530/350, 324, 857; 514/2, 12

[56] References Cited

PUBLICATIONS

G. Allen. Sequencing of proteins and peptides. NewYork: North–Holland Publishing Co. pp. 43–62, 1981.

T. Shigenaga et al., "Separation of Large and Small Granules from Horseshoe Crab(*Tachypleus Tridentatus*) Hemocytes and Characterization of Their Components" *J. Biochem.* 114:307–1316 (1993).

T. Murakami et al., "Direct Virus Inactivation of Tachyplesin I and Its Isopeptides from Horseshoe Crab Hemocytes" *Chemotherapy* 37:327–334 (1991).

M. Ohta et al., "Mechanisms of Antibacterial Action of Tachyplesins and Polyphemusins, A Group of Antimicrobial Peptides Isolated from Horseshoe Crab Hemocytes" *Antimicrobial Agents and Chemotherapy* 36:1460–1465 (1992).

T. Katsu et al., "Mode of Action of An Antimicrobial Peptide, Tachyplesin I, on Biomembranes" *Biol. Pharm. Bull.* 16(2):178–181 (1993).

N.G. Park et al., "Conformation of Tachyplesin I from *Tachypleus Tridentatus* When Interacting with Lipid Matrices" *Biochemistry* 31:12241–12247 (1992).

V.N. Korkryakov et al., "Protegrins: Leukocyte Antimicrobial Peptides that Combine Features of Corticostatic Defensins and Tachyplesins" *FEBS* 327(2):231–236 (1993).

K. Masuda et al., "Bactericidal Action of Tachyplesin I Against Oral Streptococci" *Oral Microbiol. and Immunol.* 9(2)77–80 (1994).

T. Saito et al., "A Novel Big Defensin Identified in Horseshoe Crab Hemocytes: Isolation, Amino Acid Sequence, and Antibacterial Activity" *J. Biochem.* 117:1131–1137 (1995).

T. Saito et al., "A Novel Type of Limulus Lectin–L6" *J. Biol. Chem.* 270(24):14493–14499 (1995).

*Primary Examiner*—Robert A. Wax
*Assistant Examiner*—Gabriele E. Bugaisky
*Attorney, Agent, or Firm*—Testa, Hurwitz & Thibeault

[57] ABSTRACT

The present invention relates to polypeptide having a primary structure of amino acid sequence shown by Sequence List Sequence No. 1 and DNA encoding for the polypeptide. The polypeptide is obtainable by following steps (1)–(3):

Step (1): extracting small granule fraction of homocytes of horseshoe crab with a buffer containing protein denaturing agent and chelating agent, Step (2): subjecting said extract to reverse phase high performance liquid chromatography, Step (3): eluting by concentration gradient elution with a hydrophobic organic solvent.

Also, the polypeptide is produced by chemical synthesis. The polypeptide has similar chemical structure to defensin and is useful as gargles, disinfectants, antiseptics or antimicrobials.

6 Claims, 1 Drawing Sheet

HORSESHOE CRAB HEMOCYTE POLYPEPTIDES, AND PREPARATION AND DNA ENCODING THEREOF

FIELD OF THE INVENTION

This invention relates to polypeptides having antimicrobial activities against bacteria including Gram positive and negative bacteria, and fungi, and preparation thereof and DNA encoding said polypeptides.

The polypeptides of the present invention possess potent antimicrobial activity, and thus are useful as antimicrobial, bactericidal and antiseptic agents against various microorganisms.

BACKGROUND OF THE INVENTION

Horseshoe crabs have a type of hemocyte that is filled with two kinds of granules, large and small, having different densities. The large granules contain a body fluid coagulation factor and an anti-lipopolysaccharide factor, and the small granules contain antimicrobial substances such as tachyplesin. The inventors of the present invention isolated six proteins, designated S1–S6, from the hemocytes of horseshoe crab which are components of small granules (Shigenaga, T. J. et al., J. Biochem., 114, 307–316(1993)).

A group of peptides having antimicrobial activity and generally called defensins have been previously isolated from cellular granitles of neutrophils and macrophages of mammals such as humans, rabbits, guinea pigs and rats, and their total amino acid sequences are disclosed in U.S. Pat. No. 5,242,902. The growth stimulating effect of defensins on epidermal cells and fibroblast cells is disclosed in U.S. Pat. No. 5,242,902, in addition to the antimicrobial activity against Gram negative and positive bacteria and fungi. Defensins are basic peptides having about 30 amino acid residues and the common feature of six cysteine residues and three disulfide bonds.

No polypeptide isolated from the hemocytes of horseshoe crab having a similar amino acid sequence to those of the defensins has been reported. Furthermore, no nucleotide sequence corresponding to the amino acid sequence of the polypeptide of the present invention has been reported.

The inventors of the present invention further investigated the S5 peptide fraction in the isolated components of small granule fractions of horseshoe crab hemocytes and determined its full length amino acid sequence. The amino acid sequence is similar to the sequence of the C-terminus of known defensins. Further, the antimicrobial activity of the S5 peptide fraction was found to have potent antimicrobial activities against Gram positive and negative bacteria and fungi.

SUMMARY OF THE INVENTION

One object of the present invention is to provide a DNA encoding one or more polypeptides which show significant physiological activity against Gram positive and negative bacteria and fungi.

The other object of the present invention is to provide polypeptides having the following amino acid sequence shown by the following [Formula 1].

[Formula 1]

| AA1 | AA2 | Cys | AA2 | AA2 | AA2 | AA1 | AA2 | AA4 | Cys | Arg | Ser | AA1 | Cys | Phe |
|---|---|---|---|---|---|---|---|---|---|---|---|---|---|---|
| | | | 5 | | | | | 10 | | | | | | 15 |
| Arg | AA1 | Glu | AA4 | AA2 | AA3 | AA2 | AA4 | AA4 | Ser | Ala | AA2 | Cys | Gly | Arg |
| | | | | 20 | | | | | 25 | | | | | 30 |
| Tyr | AA4 | Cys | Cys | Arg | AA2 | AA1 | | | | | | | | |
| | | | | 35 | | | | | | | | | | |

(wherein AA1 represent a basic amino acid residue, AA2 represents a neutral amino acid residue, AA3 represent an acidic amino acid residue, and AA4 represents an aromatic amino acid residue, respectively. The cysteine residues at the 3rd, 10th, 14th, 28th, 33rd and 34th positions may form disulfide bonds (—S—S—) between at least one of the following pairs: 3rd and 34th, 10th, and 28th, and 14th and 33rd positions.)

Another object of the present invention is to provide a polypeptide comprising the following amino acid sequence shown by [Formula 3].

[Formula 3]

| Asn | Pro | Leu | Ile | Pro | Ala | Ile | Tyr | Ile | Gly | Ala | Thr | Val | Gly | Pro |
|---|---|---|---|---|---|---|---|---|---|---|---|---|---|---|
| 1 | | | | 5 | | | | | 10 | | | | | 15 |
| Ser | Val | Trp | Ala | Tyr | Leu | Val | Ala | Leu | Val | Gly | Ala | Ala | Ala | Val |
| | | | | 20 | | | | | 25 | | | | | 30 |
| Thr | Ala | Ala | Asn | Ile | Arg | Arg | Ala | Ser | Ser | Asp | Asn | His | Ser | Cys |
| | | | | 35 | | | | | 40 | | | | | 45 |
| Ala | Gly | Asn | Arg | Gly | Trp | Cys | Arg | Ser | Lys | Cys | Phe | Arg | His | Glu |
| | | | | 50 | | | | | 55 | | | | | 60 |
| Tyr | Val | Asp | Thr | Tyr | Tyr | Ser | Ala | Val | Cys | Gly | Arg | Tyr | Phe | Cys |
| | | | | 65 | | | | | 70 | | | | | 75 |
| Cys | Arg | Ser | Arg | (SEQ ID NO:1) | | | | | | | | | | |

(wherein the cysteine residues at the 45th, 52nd, 56th, 70th, 75th and 76th positions may form disulfide bonds (—S—S—) between at least one of the following pairs: 45th and 76th, 52nd and 70th, and 56th and 75th positions.)

Another further object of the present invention is to provide an antimicrobial polypeptide comprising a fraction obtained by extracting the small granule fraction of hemocytes of horseshoe crab with a buffer containing guanidine and a chelating agent, subjecting the extract to reverse phase high performance liquid chromatography, and eluting by a concentration gradient with acetonitrile, said polypeptide having the following physicochemical properties:

(i) a single band by SDS-PAGE under reducing condition;
(ii) a molecular weight of about 8,200 kDa as estimated by SDS-PAGE under reducing conditions;
(iii) comprises 79 amino acids; and
(iv) antimicrobial activities against Gram negative and positive bacteria, and fungi.

A further object of the present invention is to provide a process for producing a polypeptide comprising the amino acid sequence shown in [Formula 1], which process comprises extracting the small granule fraction of hemocytes from horseshoe crab with a buffer containing a protein denaturing agent and chelating agent, subjecting the extract to reverse phase high performance liquid chromatography, and eluting with a hydrophobic organic solvent.

Figure 2:
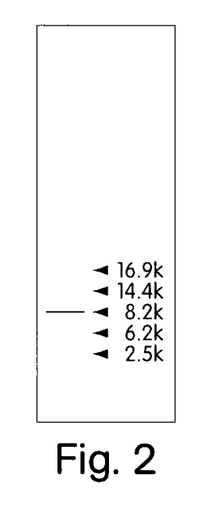
FIG. 2 shows an SDS-PAGE pattern of the polypeptide of the present invention obtained by the methods of Example 1 under reducing conditions. The pattern on the left shows the (wherein the cysteine residues at the 3rd, 10th, 14th, 28th, 33rd and 34th positions may form disulfide bonds (—S—S—) between at least one of the following pairs: 3rd and 34th, 10th and 28th, and 14th and 33rd positions.

A further object of the present invention is to provide a single stranded DNA comprising a nucleotide sequence encoding by above mentioned the polypeptide shown by above mentioned [Formula 3] or a double stranded DNA composed of said DNA and its complementary DNA.

polypeptide of the present invention and the pattern on the right shows the marker. LMW Kit 1 (Pharmacia Biosystems Co. Ltd.) was used as a marker.

DETAILED DESCRIPTION OF THE INVENTION

This invention provides polypeptides shown by following 1)–6). 1) A polypeptide having at least the following amino acid sequence shown by [Formula 1].

(wherein AA1 represents a basic amino acid residue, AA2 represents a neutral amino acid residue, AA3 represents an acidic amino acid residue, and AA4 represents an aromatic amino acid residue, respectively. The cysteine residues at the 3rd, 10th, 14th, 28th, 33rd and 34th positions may form disulfide bonds (—S—S—) between at least one combination of the 3rd and 34th, and 14th and 33rd positions.)

2) The polypeptide according to 1), wherein AA1 represents a basic L-amino acid residue selected from the group consisting of Arg, Lys and His, AA2 represents a neutral L-amino acid residue selected from the group consisting of Gly, Ala, Leu, Val, Ile, Met, Pro, Asn, Thr, Ser and Gln, AA3 represents an acidic L-amino acid residue selected from the group consisting of Asp and Glu, and AA4 represents an aromatic L-amino acid residue selected from the group consisting of Trp, Tyr and Phe in [Formula 1).

3) A polypeptide having at least the following amino acid sequence shown by [Formula 2].

A further object of the present invention is to provide a polypeptide comprising the following amino acid sequence shown by [Formula 4].

(wherein one Arg may be bound through peptide linkage to the amino terminal and the cysteine residues at the 8th, 15th, 19th, 33rd, 38th and 39th positions may form disulfide bond (—S—S—) between at least one of the following pairs: 8th and 39th, 15th and 33rd, and 19th and 38th positions).

A further object of the present invention is to provide a polypeptide comprising the following amino acid sequence shown by [Formula 5].

(wherein one Arg may be bound through peptide linkage to the carboxyl terminal.)

Further objects of the present invention will be clearly shown by the following disclosure.

4) The antimicrobial polypeptide comprising a primary structure 3) above at the carboxyl terminus hydrophobic polypeptide region at the amino terminus.

5) A polypeptide comprising the following amino acid sequence shown by [Formula 3].

-continued

Ser Val Trp Ala Tyr Leu Val Ala Leu Val Gly Ala Ala Ala Val
                20              25              30

Thr Ala Ala Asn Ile Arg Arg Ala Ser Ser Asp Asn His Ser Cys
                35              40                      45

Ala Gly Asn Arg Gly Trp Cys Arg Ser Lys Cys Phe Arg His Glu
                50              55              60

Tyr Val Asp Thr Tyr Tyr Ser Ala Val Cys Gly Arg Tyr Phe Cys
                65              70              75

Cys Arg Ser Arg (wherein the cysteine residues at the 45th, 52nd, 56th, 70th, 75th and 76th positions may form disulfide bonds (—S—S—) between at least one the following pairs: of 45th and 76th, 52nd and 70th, and 56th and 75th positions.)

6) An antimicrobial polypeptide comprising a fraction obtained by extracting the small granule fraction of hemocytes of horseshoe crab with a buffer containing guanidine and a chelating agent, subjecting the extract to reverse phase high performance liquid chromatography, and eluting by concentration gradient elution with acetonitrile, showing the following physicochemical properties.
   (i) a single band by SDS-PAGE under reducing condition;
   (ii) a molecular weight of about 8,200 kDa as estimated by SDS-PAGE under reducing conditions.
   (iii) comprises 79 amino acids; and
   (iv) antimicrobial activities against Gram negative and positive bacteria, and fungi.

This invention further provides polypeptides obtained by digestion of the polypeptide shown by [Formula 3] in 5) with a protease.

Further, this invention provides a polypeptide comprising the amino acid sequence shown in [Formula 4], and a polypeptide comprising the amino acid sequence shown in [Formula 5],

[Formula 4]

Ala Ser Ser Asp Asn His Ser Cys Ala Gly Asn Arg Gly Trp Cys
1               5               10              15

Arg Ser Lys Cys Phe Arg His Glu Tyr Val Asp Thr Tyr Tyr Ser
                20              25              30

Ala Val Cys Gly Arg Tyr Phe Cys Cys Arg Ser Arg
                35              40

(wherein one Arg may be bound through peptide linkage to the amino terminus and the cysteine residues at 8th, 15th, 19th, 33rd, 38th and 39th positions may form disulfide bond (—S—S—) between at least one the following pairs: of 8th and 39th, 15th and 33rd, and 19th and 38th positions).

[Formula 5]

Asn Pro Leu Ile Pro Ala Ile Tyr Ile Gly Ala Thr Val Gly Pro
1               5               10              15

Ser Val Trp Ala Tyr Leu Val Ala Leu Val Gly Ala Ala Ala Val
                20              25              30

Thr Ala Ala Asn Ile Arg
                35

(wherein one Arg may be bound through peptide linkage to the carboxyl terminus).

In addition, the present invention provides antimicrobial agents comprising these polypeptides or pharmacologically acceptable salts thereof as the effective ingredient.

Further, the present invention provides a single stranded DNA comprising a nucleotide sequence encoding the polypeptide shown in [Formula 3] or a double stranded DNA composed of said DNA and a complementary DNA.

Furthermore, the present invention provides a process for producing a polypeptide according to a polypeptide according to disclosed in 1)–6) above, which process comprising extracting the small granule fraction of hemocytes of horseshoe crab with a buffer containing a protein denaturing agent and a chelating agent, subjecting the extract to reverse phase high performance liquid chromatography, and eluting with a hydrophobic organic solvent.

The raw material small granule fraction of horseshoe crab hemocytes of useful in the present invention includes the small granule fraction of hemocytes obtained from the blood of horseshoe crabs, for example, *Limulus polyphemus, Tachypleus tridentatus, Tachypleus gigas* and *Carcinoscorpius rotundicauda*.

Hemocytes are separated from the blood of the horseshoe crab, and small granules are separated from the hemocytes to give the desired small granule fraction.

Practically, for example, isolated hemocytes of horseshoe crab are suspended in 0.008M Tris-HCl buffer containing 0.001M propranolol, 0.001M phenylmethanesulfonyl fluoride (PMSF) and 0.75M sucrose, pH 7.4. The suspension is shaken for a while and centrifuged to give a supernatant. The supernatant is mixed with heparin to give a final concentration of 40 USP unit/ml and centrifuged. The upper layer is harvested and centrifuged using 1.5–2.4M sucrose density gradient solution containing 0.008M Tris-HCl buffer (pH 7.4), 0.001M PMSF and heparin (40 USP unit/ml) at 112,000×g for 30 min. The separated lower layer is collected and used as the small granule fraction.

The obtained small granule fraction of hemocytes of horseshoe crab is ① sonicated in a suitable buffer such as 0.02M Tris-HCl buffer containing 6M guanidine and 0.002M ethylenediaminetetraacetic acid (EDTA), pH 8.0, and extracted after the incubation at 37° C. for one hr., ② the extract is subjected to reverse phase HPLC using TSK gel Phenyl 5PW-RP (TOSOH Corp.) as a carrier and eluted by a concentration gradient of acetonitrile to give the S5fraction of antimicrobial polypeptide of the present invention.

The eluted fraction, S5, obtained by the reverse phase HPLC in step ② may be further purified by reverse phase HPLC using TSK gel ODS120T (TOSOH Corp.) as a carrier. The determination of peptide content during the purification process can be carried out by measuring the ultraviolet absorption at a wave length of 214 nm.

The polypeptides of the present invention can be prepared by well known processers, for example, solution or solid phase syntheses (Nobuo Izumiya, Tetsuo Kato, Haruhiko Aoyagi and Michinori Waki, "Fundamentals and Experiments of Peptide Synthesis", 1985, Pub. by Maruzen Co., Ltd.). For example, preparation of the polypeptide chain of [Formula 1] having an Arg residue at position 37 in the amino acid sequence by a solid phase synthetic method is carried out by direct or indirect coupling via a spacer of the carboxyl group of the N-protected arginine to an insoluble resin having a chloromethyl or hydroxymethyl group, then coupling in a stepwise manner the 36th to 1st protected amino acids by the solid phase synthetic method and. eliminating the insoluble resin and the protecting group to give the polypeptide chain of [Formula 1]. Further, the three pairs of cysteine residues at the 3rd and 34th, 10th and 28th, and 14th and 33rd position of the obtained polypeptide may form the respective disulfide bond independently through their mercapto groups.

These disulfide bonds may be formed by well known methods, for example by mild air oxidation.

The insoluble resin having the chloromethyl or hydroxymethyl group and spacer used for the synthesis of the polypeptides of the present invention, in some cases N-protected amino acid resins prepared by coupling N-protected amino acid with insoluble resin, can be prepared by known methods and various types of the insoluble resin, the spacer, and the N-protected amino acid coupled insoluble resins are commercially available.

Any insoluble resins which can directly, or occasionally via a spacer, coupled with the carboxyl group of the C-terminal N-protected amino acid, and then are removable from the carboxyl group can be used for the present invention. Useful insoluble resins are, for example, chloromethyl resin (chloromethylated styrene - divinyl-benzene copolymer), hydroxymethyl resin or 4-hydroxymethyl-Pam (phenylacetamidomethyl)-resin with spacer for Boc (t-butyloxycarbonyl) strategy, and hydroxymethylphenoxymethyl resin (Wang) resin and their derivatives for Fmoc (9-fluorenylmethyloxycarbonyl) strategy.

The protected amino acids are amino acids having a functional group which is protected by a protecting group by known methods. Various protected amino acids are commercially available. For the synthesis of polypeptides of the present invention, the below mentioned protecting groups are preferred. The protecting groups of α-amino group of amino acid include Boc (t-butyloxyclarbonyl) and Fmoc (9-fluorenylmethyloxycarbonyl) groups. The protecting groups of the guanidino group of arginine (Arg) include Tos (tosyl), $No_2$ (nitro), Mtr (4-methoxy-2, 3, 6-trimethyl-benzene-sulfonyl), and Pmc (2, 2, 5, 7, 8-pentamethylchroman-6- sulfonyl) groups. The protecting groups of the ε-amino group of lysine (Lys) include Z benzyloxycarbonyl), Cl.Z (2-chlorobenzyl-oxycarbonyl), Boc, and Npys (3-nitro-2-pyridinesulfenyl) groups. The protecting groups of the imidazolyl group of histidine (His) include Tos, Z, Pac (phenacyl), Bom (benzyloxymethyl), Dnp (dinitrophenyl) and Trt (trityl) groups. The protecting groups of the mercapto group of cysteine (Cys) include Bzl (benzyl), MBzl (4-methoxybenzyl), 4-MeBzl (4-methylbenzyl), Acm (acetamidomethyl), Trt, Npys, t-Bu (t-butyl) and t-BuS (t-butylthio) groups, and MBzl, 4-MeBzl, Trt, Acm and Npys groups are preferably used. The protecting groups of the hydroxy groups of tyrosine (Tyr) include Bzl, C12.Bzl (2, 6-dichlorobenzyl) and t-Bu groups, but tyrosine may be used without protection. The protecting groups of the indole group of tryptophan (Trp) includes a CHO (formyl) group but tryptophan may be used without protection. The protecting groups of the thiomethyl group of methionine (Met) includes methylsulfoxide group but methionine may be used without protection. The protecting groups of hydroxy group of the serine (Ser) and threonine (Thr) include Bzl and t-Bu groups. The protecting groups of the carboxyl group of aspartic acid (Asp) and glutamic acid (Glu) include OBzl (benzyl ester), OtBu (t-butyl ester), OcHex (cyclohexyl ester) and OPac (phenacyl ester) groups. The protecting groups of the carbamide group of asparagine (Asn) and glutamine (Gln) include Trt and Xan (xanthyl) groups.

Each protecting group is selected from known protecting groups according to the reaction conditions for peptide synthesis.

The coupling of the protected amino acids is carried out by conventional condensation methods, for example, methods of DCC (dicyclohexylcarbodiimide), DIPCDI (diisopropyl-carbodiimide) [Tartar, A., et al.; J. Org. Chem., 44, 5000 (1979)], active ester, mixed or symmetric acid anhydride, carbonyldiimidazole, DCC-HOBt (1-hydroxybenzotriazole) [Keonig,W., et al.: Chem. Ber., 103, 788, 2024, 2034 (1970)], diphenyl phosphoryl azide, BOP-HOBt using BOP reagent (benzotriazolyl-N-hydroxy tris(dimethyl-amino)phosphonium hexafluorophosphate) (Hudson, D., J. Org. Chem., 53, 617 (1988)), HBTU (2-(1H)-benzotriazol-1-yl)-1 1, 3, 3-tetramethyluronium hexafluorophosphate)-HOBt (Knorr, R., et al., Tetrahedron Lett., 30, 1927 (1989)) and TBTU (2-(lH)-benzotriazol-l-yl)-l, 1, 3, 3-tetramethyluronium tetrafluoroborate)-HOBt (Knorr, R., et al. Tetrahedron Lett., 30, 1927 (1989)). However, methods of DCC, DCC-HOBt, BOP-HOBt, HBTU-HOBt and symmetric acid anhydride are preferably used.

These condensation reactions are generally carried out in an organic solvent such as dichloromethane, dimethylformamide (DMF) and N-methylpyrrolidone (NMP) or mixtures thereof.

The eliminating reagents of the protecting group of the α-amino group include trifluoroacetic acid/dichloromethane, HCl/dioxane, piperidine/DMF and piperidine/NMP, and are suitably selected according to the properties of the protecting group to be eliminated.

The progress of the condensation reaction in the respective synthetic steps is monitored by the ninhydrin reaction method of Kaiser, E., et. al. [Anal. Biochem., 34, 595 (1970)].

The protected peptide resins having the desired amino acid sequences can be obtained by the methods shown above.

The protected peptide resins are treated with HF, TFMSA (trifluoromethanesulfonic acid) (Yajima, H., et al.; "The Peptides" 5, 65 (1983), ed. by Gross, E., pub. by Academic Press), TMSOTf (trimethylsilyl triflate) [Fujii, N., et al.; J. Chem. Soc., Chem. Commun., 274 (1987)], TMSBr (trimethylsilyl bromide) [Fujii, N., et al., Chem. Pharma. Bull., 35, 3880 (1987)] or trifluoroacetic acid (TFA) to simultaneously eliminate the resins and protecting groups. The above mentioned eliminating reagents are suitably selected according to the strategy (Boc or Fmoc), resins and protecting groups, respectively.

The resultant peptides can be reduced with a reducing agent such as 2-mercaptoethanol and DTT (dithiothreitol) to secure the reduced form of mercapto group of the cysteine, and the mercapto groups are oxidized to give cyclic peptides with disulfide (—S—S—) bond.

The oxidizing treatment can be performed by well known methods and generally oxygen in the air or an oxidizing agent such as ferricyanate (for example potassium ferricyanate) is used.

The resultant polypeptides are isolated and purified by known methods in the field of peptide chemistry, for example, extraction, recrystallization, various chromatographies (such as gel filtration, ion exchange, partition, absorption and reversed phase chromatography), electrophoresis, and counter current distribution. Among them, reversed phase high performance liquid chromatography (HPLC) is most effective.

The symbols used for the amino acid residues of polypeptides in the specification of the present invention are expressed by the internationally authorized three letter symbols. That is, each symbol represents the below mentioned amino acid residue, respectively.

| His; | histidine, | Ser; | serine, | Cys; | cysteine, |
|---|---|---|---|---|---|
| Ala; | alanine, | Gly; | glycine, | Asn; | asparagine, |
| Arg; | arginine, | Trp; | tryptophan, | Lys; | lysine, |
| Phe; | phenylalanine, | Glu; | glutamic acid, | Tyr; | tyrosine, |
| Val; | valine, | Asp; | aspartic acid, | Thr; | threonine, |
| Leu; | leucine, | Ile; | isoleucine, | Met; | methionine, |
| Pro; | proline, | Gln; | glutamine | | |

Cysteine residues without formation of disulfide bonds, or those obtained by reduction of disulfide bonds by known methods such as reduction with a reducing agent, e.g., dithiothreitol, may be carboxymethylated with known methods such as reaction with iodoacetic acid to give carboxymethylated polypeptide derivatives of the present invention. These carboxymethylated polypeptide derivatives also exhibit potent antimicrobial activity against Gram negative and positive bacteria.

The fractions of polypeptides of the present invention can be obtained by degradation of the polypeptide shown by above mentioned [Formula 3] of the present invention with conventional methods using a protease such as trypsin, chymotrypsin or pepsin. The resultant polypeptides may be isolated and purified by known methods in the field of peptide chemistry, and among them reversed phase HPLC is most effective.

According to the present invention, a DNA (AAT to CGC; nucleotide sequence Nos. 135–371) encoding the polypeptide shown by amino acid sequence (Asn to Arg; amino acid Nos. 179) in [Formula 3] (Sequence Table, Sequence No. 5) can be obtained. In addition, DNAs encoding for polypeptides of [Formula 2], [Formula 4] and [Formula 5] each having a common amino acid sequence region with that of polypeptide of [Formula 3] can be obtained by a similar method.

That is, an oligonucleotide is synthesized based on the partial amino acid sequences of the polypeptide shown in [Formula 3]. cDNAs encoding said polypeptide are isolated from a cDNA library, which is prepared from poly(A)+RNA isolated from horseshoe crab hemocytes, using said oligonucleotides or antibodies against polypeptide. The nucleotide sequences of these cDNA can be confirmed using dideoxy chain termination method (Sanger, F., et al., Proc. Natl. Acad. Sci., U.S.A. 74, 5463–5467 (1977)) to give the DNAs of the present invention. Furthermore, the amino acid sequences of the polypeptides can be determined from the nucleotide sequences and above mentioned partial amino acid sequences. In addition, with regard to the nucleotide sequence in the region encoding the polypeptide, DNAs obtained by substitution to give other codons which correspond to the same amino acid are included within the scope of the present invention.

Further, the polypeptides of the present invention can be prepared by the following procedures using DNAs of the present invention.

DNAs encoding for the peptides of the present invention obtained by the above mentioned procedure are cleaved by ultrasonic treatment or restriction enzymes, or other methods known to the field of gene technology, and subcloned into a suitable vector. The subcloned vectors are transfected into suitable host organisms or cells to give transformants. The transformants are bred or cultured by suitable conditions to stably produce a large amounts of polypeptides. The conditions for selection and culture of transformants can be suitably selected from the conditions known for the production of polypeptides, depending on the growth requirements of the hosts used. The desired polypeptides can be obtained by protein isolation and purification procedures well known in the field of gene technology and protein chemistry.

The polypeptides of the present invention exhibit base characteristics due to their amino acids composition and form salts with acids. For example, the polypeptides form salts with inorganic acids, e.g., hydrochloric acid, hydrobromic acid, phosphoric acid, nitric acid and sulfuric acid, organic carboxylic acids, e.g., acetic acid, propionic acid, maleic acid, succinic acid, malic acid, citric acid, tartaric acid and salicylic acid, acidic sugars, e.g., glucuronic acid, galacturonic acid, gluconic acid and ascorbic acid, acidic polysaccharides, e.g., hyaluronic acid, chondroitin sulfate and alginic acid, or organic sulfonic acid, e.g., methanesulfonic acid and p-toluenesulfonic acid. The polypeptides of the present invention can be used as medicinally acceptable salts thereof.

The polypeptides and salts thereof of the present invention can be used as gargles, disinfectants, antiseptics and antimicrobials in the forms of compositions composed of the said polypeptides and salts thereof as an effective ingredient and pharmaceutically acceptable carriers selected according to the methods and forms of administration. That is, gargles, disinfectants, antiseptics and antimicrobials composed of an effective ingredient of the polypeptides of the present invention can be used, according to the treatment or disinfection method of infected sites including out side and inside of the body, parenterally as external preparations, injection preparations and suppositories, or orally with suitable pharmaceutical carriers according to the methods of administration in the form of preparations such as powder granules, solutions for injection or oral administration, tablets, suppositories, pessaries, ointments, creams and aerosols.

When the antimicrobials composed of polypeptides of the present invention as effective ingredients are directly administered as injection preparations to a body, the polypeptides or salts thereof of the present invention may be dissolved in a saline solution and successively or intermittently administered by drip infusion or intravenous injection.

Furthermore, the polypeptides of the present invention contain an amino acid sequence similar to that of defensin, thus, wound healing effect is expected.

The dose of the polypeptides of the present invention vary with the symptoms, genders and ages of the patients, and route of administration. The parenteral daily dose for an adult patient is 0.2–20 mg as a gargle or an antimicrobials by an above mentioned administration method in several administrations. The polypeptides of the present invention can be orally administered at daily doses of 2–200 mg in several administrations.

The present invention will be practically explained by the following examples.

[EXAMPLE 1]

(1) Preparation of the small granule fraction of hemocytes of horseshoe crab.

Figure 1:
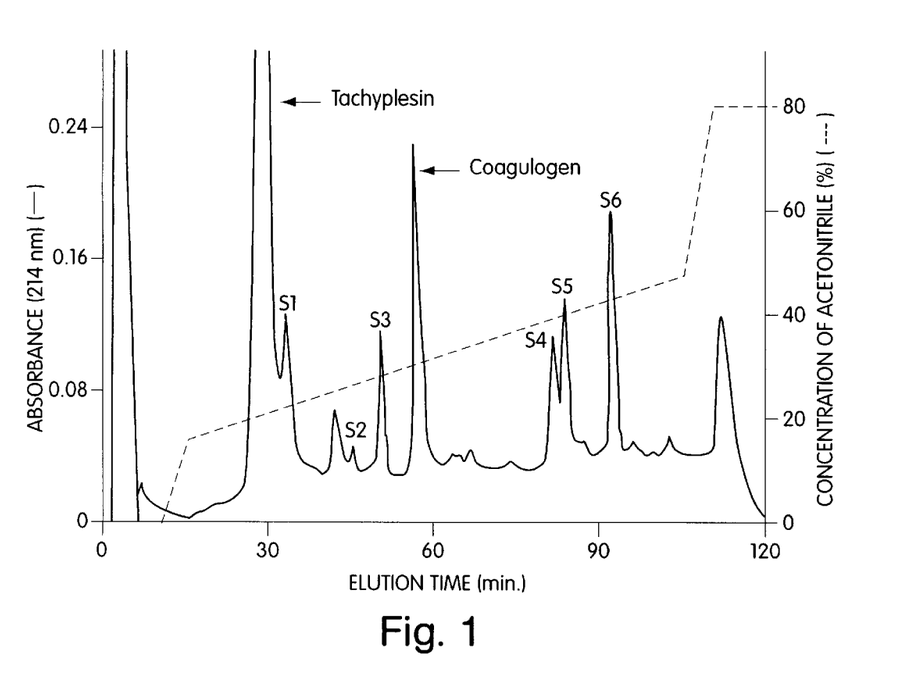
FIG. 1 shows an elution curve of the polypeptide of the present invention from TSK gel Phenyl 5PW-RP column by concentration gradient elution with the acetonitrile method described by Example 1.

In 100 ml of hemocyte of Tachypleus tridentatus, 100 ml of 3% NaCl aqua containing 0.002M propranolol was added and allowed to stand for 15 min. on ice and centrifugedat 150×g for five min. at 4° C. to precipitate the hemocytes. The were resuspended in 20 ml of 0.008M Tris-HCl buffer containing 0.001M propranolol, 0.001M PMSF and 0.75M sucrose, pH 7.4, gently mixed and centrifuged at 400×g for 15 min. at 4° C. Heparin was added to the resultant supernatant to give 40 USP unit/ml solution, centrifuged at 400 ×g for 10 min. at 40° C., 5 ml of the upper layer containing granule fraction was layered on top of 8 ml of 1.5–2.4M sucrose density gradient solution containing 0.008M Tris-HCl buffer, pH 7.4, 40 USP units/ml of heparin and 0.001M PMSF, and centrifuged at 112,000 ×g for 30 min. at 4° C. to form two layers. The lower layer containing the small granule fraction was obtained. (2) Preparation of the antimicrobial polypeptide In 3 ml of the small granule fraction, 1 ml of a mixed solution of chloroform-methanol (1:4) was added, and centrifuged to form a precipitate. The precipitate was mixed with 0.05M Tris-HC1 buffer containing 6M guanidine and 0.002M EDTA, pH 8.0, ultrasonicated at 1OW for 10 sec, placed at 37° C. for 1 hr., then centrifuged. The resultant supernatant was applied to a TSK gel Phenyl 5PW-RP (TOSOH Corp.) column of 4.6×75 mm previously equilibrated with 0.1 v/v % trifluoroacetic acid (TFA) and the adsorbed polypeptide was gradient eluted with 0.1% TFA solution containing 16∼48 v/v % of acetonitrile with continuous elevation of concentration, at a flow rate of 0.5 ml/min. under monitoring with UV absorption at 214 nm. The results are shown in FIG. 1. The S5 fraction shown in FIG. 1 was applied to the TSK gel ODS120T (TOSOH Corp.) column of 4.6×150 mm previously equilibrated with 0.1% TFA and the column was eluted with 0–80 v/v % of acetonitrile, with continuous increase in concentration, using a linear gradient elution at a flow rate of 0.5 ml/min. to yield purified S5 fraction of polypeptide.

The resultant polypeptide was subjected to SDS-PAGE and formed a single band with a calculated mass of about 8,200 kDa under reducing condition as shown in FIG. 2.

[EXAMPLE 2]

(Amino acid analysis and determination of amino acid sequence)

The purified polypeptide obtained by Example 1 was applied to a TSK gel Phenyl 5PW-RP (TOSOH Corp.) column of 4.6×75 mm previously equilibrated with 0.1 v/v % TFA, the column was washed thoroughly and eluted using a linear gradient elution with acetonitrile at a concentration of 8 v/v % at 10 min., 16 v/v % at 15 min., 48 v/v % at 105 min., and 80 v/v % at 110 min., at a flow rate of 0.5 ml/min. to elute the adsorbed polypeptide. During elution the concentration of polypeptide was monitored by UV absorption at 214 nm to give fractions with a high concentration of the polypeptide.

The obtained polypeptide was hydrolyzed with 5.7M HCl for 24, 48 and 72 hrs. or with 4M methanesulfonic acid to determine the amino acid composition. The result is shown in Table 1. The amino acid composition determined by amino acid analysis approximately agreed with theoretical values calculated from the amino acid sequence shown by [Formula 3].

TABLE 1

| Amino Acid | Found[a] (Number of residue/ molecule) | Calculated (Number of residue/ molecule) |
|---|---|---|
| Asp | 6.0 | 6 |
| Thr | 3.2 | 3 |
| Ser | 7.0 | 7 |
| Glu | 1.3 | 1 |
| Pro | 4.0 | 3 |
| Gly | 6.1 | 6 |
| Ala | 12.0 | 12 |
| ½ Cys[b] | 4.7 | 6 |
| Val | 6.7 | 7 |
| Met | 0 | 0 |
| Ile | 3.7 | 4 |

TABLE 1-continued

| Amino Acid | Found[a] (Number of residue/ molecule) | Calculated (Number of residue/ molecule) |
|---|---|---|
| Leu | 3.1 | 3 |
| Tyr | 5.7 | 6 |
| Phe | 1.9 | 2 |
| Lys | 1.9 | 1 |
| His | 1.8 | 2 |
| Trp[c] | 1.8 | 2 |
| Arg | 7.5 | 8 |
| Total | | 79 |

[a] The mean values after hydrolysis with 5.7M HCl at 110° C. for 24, 48 and 72 hrs. The values for Ser and Thr were obtained by extrapolation to 0 (zero) hr.
[b] Determination as cysteric acid given by performic acid oxidation with formic acid and hydrogen peroxide, followed by hydrolysis for 24 hrs.
[c] Determination by 4M methanesulfonic acid method.

Determination of amino acid sequence of the resulted polypeptide by gas phase Edman degradation (Applied Biosystems Co., Ltd., Type 477A) gave the following amino acid sequence (Sequence Table, Seq. No. 1) shown in [Formula 3].

[Formula 3]

Asn Pro Leu Ile Pro Ala Ile Tyr Ile Gly Ala Thr Val Gly Pro
                5              10                 15
Ser Val Trp Ala Tyr Leu Val Ala Leu Val Gly Ala Ala Ala Val
              20                 25                 30
Thr Ala Ala Asn Ile Arg Arg Ala Ser Ser Asp Asn His Ser Cyc
              35                 40                 45
Ala Gly Asn Arg Gly Trp Cys Arg Ser Lys Cys Phe Arg His Glu
              50                 55                 60
Tyr Val Asp Thr Tyr Tyr Ser Ala Val Cys Gly Arg Try Phe Cys
              65                 70                 75
Cys Arg Ser Arg

[EXAMPLE 3]

The apparatuses and reagents used in the below mentioned example are as follows:

Medium pressure column chromatography apparatus:
Yamazen Co., Ltd., Preparative Medium Pressure Liquid Chromatograph Type YFLC-6004-FC-6R
Column used for the above apparatus:
SepPak C18 (Waters Ltd. (U.S.A.)), packed column
Peptide Synthesizer: Applied Biosystems Co., Ltd. (U.S.A.)
Type 430A
Amino Acid Analyzer: Hitachi Ltd.
Hitachi High Speed Amino Acid Analyzer Type L-8500
Fmoc amino acids: Peptide Research Inst. and Watanabe Chemical Co., Ltd.
Resins for Solid Phase Synthesis: Peptide Research Inst. and Watanabe Chemical Co., Ltd.
Coupling agents: Peptide Research Inst., Watanabe Chemical Co., Ltd. and Applied Biosystems Japan Co., Ltd.
Reagents for elimination of protecting group: Peptide Research Inst. and Watanabe Chemical Co., Ltd.
Sephadex G10 carrier: Pharmacia Biotech Co., Ltd.

Preparation of the following polypeptide [Formula 6] by solid phase synthesis.

[Chemical formula 1]

Tyr-Phe-Cys-Cys-Arg-Ser-Arg    [Formula 6]

(wherein, His, Ser, Cys, Ala, Gly, Asn, Arg, Trp, Lys, Phe, Glu, Tyr, Val, Asp and Thr represent the aforementioned amino acid residues, and solid lines between the 3rd and 34th, 10th and 28th, and 14th and 33rd represent disulfide bonds.

The $N^\alpha$-Fmoc group removed protected peptide-Wang resin was prepared using an Automatic Peptide Synthesizer (Peptide Synthesizer: Applied Biosystems Co., Ltd. (U.S.A.)) by a solid phase synthetic method with Fmoc strategy. Synthetic process and its control was followed by the FastMoc Program developed by Applied Biosystems Co., Ltd. (U.S.A.). This FastMoc Program adopts HBTU-HOBt method which provides a rapid and a highly efficient condensation reaction.

1) Starting material, Fmocamino acid resin: Commercial FmocArg(Pmc)-Wang resin (Watanabe Chemical Co., Ltd.), in which the protected Arg at residue 37 was introduced into hydroxymethyl-phenoxymethyl resin (Wang resin), was used.

2) Introduction of the 36th Ser; FmocArg(Pmc)-Wang resin (1.25 g, 0.25 mmol; 0.2 mmol Arg/g FmocArg(Pmc)-Wang resin) and FmocSer(tBu) (383 mg, 1.00 mmol; four equivalents) were placed in a reaction vessel and Fmoc-amino acid cartridge, respectively, and were attached to the above described Automatic Peptide Synthesizer and the automatic synthetic procedure of FastMoc program was performed. The operating procedure for one cycle of synthetic reaction by the program is shown below.

TABLE 2

| Operation | Reagent | Solvent | Time × repeated times |
|---|---|---|---|
| Removal of Fmoc group | 20% piperidine/NMP | NMP | 3 min. × 1, 12 min. × 1 |
| Washing | — | NMP | 1 min. × 5 |
| Condensation reaction | Fmoc amino acid (4.0 eq) + HBTU + HOBT + DIEA* | NMP –DMF | 30 min. × 1 |
| Washing | — | NMP | 1 min. × 7 |

Required time for one cycle: 55 min.
Volume of wasted solution for one cycle: 160 ml
*Diisopropylethylamine 3) Introduction of the 35th to the 1 st positions of amino acids;
In a similar manner as shown above, Nα-Fmoc protected Arg(Pmc), Cys(Trt), Cys(Trt), Phe, Tyr(tBu), Arg(Pmc), Gly, Cys(Trt), Val, Ala, Ser(tBu), Tyr(tBu), Tyr(tBu), Thr (tBu), Asp(OtBu), Val, Tyr(tBu), Glu(OtBu), His(Trt), Arg (Pmc), Phe, Cys(Trt), Lys(Boc), Ser(tBu), Arg(Pmc), Cys (Trt), Trp, Gly, Arg(Pmc), Asn(Trt), Gly, Ala, Cys(Trt), Ser(tBu) and His(Trt) residues were successively introduced into Wang resin according to the sequence from the C-terminus and Nα-Fmoc removed protected peptide Wang resin (3.31 g) was obtained with almost 1 00% yield.

4) Preparation of the peptide by deprotection of the protecting group, removal of resin and partial purification;
Nα-Fmoc removed the protected peptide resin prepared by the procedures of aforementioned steps 1) to 3) was reacted with IM TMSOTf-thicanisole/TFA system (10 ml of TFA in the presence of mcresol (100 eq), ethanedithiol (300 eq)) per 100 mg of the peptide resin at 25° C. for 2 hrs. The reaction mixture was filtered to remove the resin and, washed twice with 1 ml of TFA. To combined filtrate and washings, 100 ml of ice cold dried ether was added, and the produced precipitate was centrifuged. The precipitates were decanted and washed with cold ether and dissolved in 10 ml of 4N acetic acid (AcOH). The solution was mixed with 830 mg of dithiothreitol (80 eq) and stirred overnight at room temperature.

The reaction mixture was centrifuged and the supernatant was applied to Sephadex G10 column of 3.7×50 cm and gel filtered with 4N AcOH. The main eluate fractions passed through the column were collected and lyophilized to yield a powder of partially purified uncyclized polypeptide of [Formula 2].

5) Preparation of polypeptide [Formula 6] (SEQ. ID NO: 8) by air oxidation:
An aqueous solution of the partially purified un-cyclized polypeptide obtained above was adjusted to pH 7.5 with concentrated ammonia water and oxidized by aeration for cyclization. After completion of air oxidation, the reaction mixture containing oxidized cyclic polypeptide was charged to 10 g of Diaion HP-20 resin and eluted with 60% acetonitrile ($CH_3CN$) in 1N AcOH. The eluate was concentrated under reduced pressure at room temperature to remove $CH_3CN$ and pulverized by lyophilization.

The lyophilized powder was dissolved in a small amount of water and applied to a SepPak medium pressure column (24×190 mm) and eluted by gradient elution with acetonitrile in 0.1% TFA aqueous solution monitoring by absorption at 280 nm for partial purification to give the desired fraction with purities of 40–50%. The desired fractions were collected, evaporated under reduced pressure, and lyophilized to give a powder. The powder product was dissolved in a small amount of water and applied to an Asahi Pack ODP-90 column (2.15×30cm) (Asahi Chemical Industry Co., Ltd.) attached to the HPLC system. The column was eluted by gradient elution with $CH_3CN$ and purified by the HPLC (TOSOH Corp., Full Automatic HPLC, Type HLC-8070) to give a single peak of the desired peptide [Formula 6] in a yield of 13%, calculated based on protecting group-protected peptide resin.

6) Analysis of the polypeptide:
The polypeptide purified by the above process 5) was subjected to acid hydrolysis with 4M methanesulfonic acid containing 0.2% tryptamine at 115. C for 24 hrs. according to the method of Liu et al. (Liu, T. Y. et al., J. Biol. Chem., 2U, 1936 (1976) to determine the amino acid composition. The composition satisfactorily agreed with that calculated from the amino acid sequence of aforementioned [Formula 6].

An analytical reversed phase HPLC profile of the polypeptide (Shimadzu Co., Ltd., HPLC Type LC-6AD; TSK ODS-120T (TOSOH Corp., 0.46×15 cm) column and TSK ODS-120T guard column (0.32×1.5 cm)) showed a single peak at 22.8 min.

Control samples of the antimicrobial peptide tachyplesin I (Nakamura, H. et al., J. Biol. Chem., 263, 16709 (1988))

and anti-HIV active peptide T22 (Nakashima, H. et al. Antimicrobial Agents and Chemotherapy, 36, 1249 (1992) ) on the above analytical reverse phase HPLC showed elution time of 24.1 and 17.2 min., respectively.

The conditions of the analytical reversed phase HPLC are as follows: two gradient eluting solutions of 0.1% TFA aqueous solution containing 10% $CH_3CN$ (A solution) and 0.1% TFA aqueous solution containing 80% $CH_3CN$ (B solution); gradient elution with mixtures of 0% of B solution at one min. and 42% of B solution at 29.4 min. at column temperature of 40° C.; flow rate of 0.8 ml/min.; detection wave length of 220 and 280 nm, and sample injection volume of 20 Ul at a peptide concentration of 0.1 mg/ml.

[EXAMPLE 4]

(Determination of antimicrobial activity)

Various microorganisms shown in Table 3 were suspended in 10 mM phosphate buffer, pH 7.0 (hypotonic solution). In 900 μl of 5,000–10,000 CFU/ml suspension (CFU, colony forming unit), 100 μl of 2-fold serially diluted polypeptide solution at a concentration of 20 μg/ml obtained by the method of Example 1 was added and incubated at 37° C. for 1 hr. Then, 100 μl of incubated mixture was inoculated in an agar medium, cultured at 37° C. for 12 hrs. and the number of colonies was counted with the naked eye (see infection and Immunity, 42, 1014 (1983)).

The results are shown in Table 3. As clearly shown in Table 3, the polypeptide of the present invention exhibited potent antimicrobial activity against Gram negative and Gram positive bacteria, and fungi.

TABLE 3

| Microorganisms | $IC_{50}$ (μg/ml) (hypotension) |
|---|---|
| Gram negative bacteria | |
| *Escherichia coli* | 2.5 |
| *Salmonella typhimurium* LT2(S) | 20 |
| *S. minnesota* Re | <0.6 |
| *Klebsiella pneumoniae* | <1.3 |
| Gram positive bacterium | |
| *Staphylococcus aureus* | <2.5 |
| Fungus | |
| *Candida albicans* | 10–20 |

[EXAMPLE 5]

In 50 mM Tris-HCl buffer, pH 8, two mg of purified polypeptide obtained by the method of Example 1 and 20 μg of trypsin (Sigma Co., Ltd.) were added and incubated at 37° C. for 24 hrs. to degrade and to yield polypeptide fractions. The degraded mixture was applied to a YMC-Pack 5C4 (YMC Co., Ltd.) column (4.6–150 mm) previously equilibrated with 0.06 v/v % TFA and eluted with 0.052% TFA solution containing gradiently elevated 0–80 v/v % $CH_3CN$ at 5–55min. at a flow rate of 0.5 ml/min. to give polypeptide fractions. The eluate was monitored with a UV absorption rate at 210 nm and fractions with high peptide concentration were collected at 27 and 47.6 min. to give two polypeptide fractions. The resultant fractions were referred to as T3 and T6 polypeptide fractions, respectively.

The two polypeptide fractions were hydrolyzed with 5.7M HCl at 110° C. for 24 hrs. and the amino acid composition was determined. The results are shown in Table 4. The determined amino acid compositions of the polypeptide fractions T3 and T6 were approximately agreed with theoretical compositions calculated from [Formula 4] and [Formula 5] (Sequence Table, Seq. Nos. 3 and 4).

TABLE 4

| | Polypeptide | | | |
|---|---|---|---|---|
| | Fraction T3 | | Fraction T6 | |
| Amino acid | Anal. (residue No./molecule) | Calcd. | Anal. (residue No./molecule) | Calcd. |
| Asp | 4.0 | (4) | 1.9 | (2) |
| Thr | 1.1 | (1) | 2.3 | (2) |
| Ser | 5.0 | (6) | 1.2 | (1) |
| Glu | 1.2 | (1) | — | — |
| Pro | — | — | 2.8 | (3) |
| Gly | 3.4 | (3) | 3.3 | (3) |
| Ala | 3.4 | (3) | 9.5 | (9) |
| ½Cys | N.D. | (6) | N.D. | (0) |
| Val | 2.1 | (2) | 5.2 | (5) |
| Met | — | — | — | — |
| Ile | — | — | 3.8 | (4) |
| Leu | — | — | 3.0 | (3) |
| Tyr | 4.0 | (4) | 2.1 | (2) |
| Phe | 1.5 | (2) | — | — |
| Lys | 1.0 | (1) | — | — |
| His | 2.0 | (2) | — | — |
| Trp | N.D. | (1) | N.D. | (1) |
| Arg | 6.7 | (6) | 1.6 | (2) |
| Total | | (42) | | (37) |

[EXAMPLE 6]

(Antimicrobial activity)

*Escherichia coli* was suspended in 10 mM phosphate buffer, pH 7.0, at a concentration of 10,000 CFU/ml and 450 μl of the suspension was mixed with 50 μl of polypeptide fraction T3(polypeptide of [Formula 4]), T6 (polypeptide of [Formula 5]), and a polypeptide obtained by Example 1 each having a concentration of 40 μg/ml, or, as a control, 10 mM phosphate buffer, pH 7.0. The mixtures were incubated at 37° C. for 1 hr. Then, 100 μl of incubated mixture was inoculated in an agar medium, cultured at 37° C. for 12 hrs. and the number of colonies were counted. Polypeptide fractions T3 (polypeptide of [Formula 4]) and T6 (polypeptide of [Formula 5]), and a polypeptide obtained by the method of Example 1 inhibited the growth of *Escherichia coli* at a rate of about 90%, about 20% and about 95% or over, respectively.

In addition, *Staphylococcus aureus* was suspended in 10 μμphosphate buffer, pH 7.0, at a concentration of 5,000 CFU/ml and 450 μl of the suspension was mixed with 50 μl each of polypeptide fraction T3 (polypeptide of [Formula 4]), T6 (polypeptide of [Formula 5]), and a polypeptide obtained by the method of Example 1 each having a concentration of 40 μg/ml and, as a control, 10 mM phosphate buffer, pH 7.0. The mixtures were incubated at 37° C. for 1 hr. Then, 100 μl of incubated mixture was inoculated in an agar medium, cultured at 37° C. for 12 hrs. and the number of colonies were counted. Polypeptide fraction T3 (polypeptide of (Formula 4]) and T6 (polypeptide of [Formula 5]), and a polypeptide obtained by the method of Example 1 inhibited the growth of Staphylococcus aureus at a rate of about 30%, about 70% and almost completely, respectively.

As clearly shown by these results, the polypeptide fractions of the present invention exhibited potent antimicrobial activity against Gram negative and Gram positive bacteria, particularly, polypeptide fraction T3 (polypeptide of [Formula 4]) and T6 (polypeptide of [Formula 5]) exhibited potent antibacterial activity against Gram negative bacteria Escherichia coli and Gram positive bacteria staphylococcus aureus; respectively.

[EXAMPLE 7]

[Preparation of DNA encoding polypeptides]

1. Synthesis of an oligonucleotide

His-Glu-Tyr-Val-Asp-Thr (Sequence table, Seq. I.D. No. 1, amino acid Nos. 59–64) in the amino acid sequence determined by the method of Example 2 was reverse translated as an antisense DNA. A mixture of oligonucleotides composed of 25 base pairs having the recognition sequence of the restriction enzyme (EcoR 1) and two bases for the protection of DNA at the 5'-terminus was synthesized using a DNA synthesizer 380A (Applied Biosystems Japan Co., Ltd.).

```
3'-GTACTTATACATCTATGCTTAAGGA-5'                [Formula 7]
     G  C   G   C  G
              A
              G                          (SEQ. ID NO:9)
```

The oligonucleotide shown here includes all possibilities of the complementary sequence to a nucleotide sequence which was reverse translated from His-Glu-Tyr-Val-Asp-Thr (however, a 5'-terminal nucleotide (T/G/C/A) of a complementary nucleotide sequence (3'-TG(T/G/C/A)-5') in codon of Thr was excluded.

2. Preparation of poly(A)⁺RNA containing mRNA encoding for a polypeptide

Poly(A)⁺ RNA was isolated from horseshoe crab hemocytes, since the polypeptide of the present invention is obtained and purified from hemocytes of horseshoe crab.

(1) Preparation of total RNA

By using of AGPC method (see Experimental Medicine (Jikken Igaku) 9, 1937–1940 (1991), Pub. by Yodosha Co., Ltd.), about 11 mg of total RNA was isolated from 11.8 g of limulus hemocytes.

(2) Preparation of poly(A)⁺ RNA

Poly(A)+RNA was isolated from about 2 mg of the above mentioned total RNA with Oligotex-dT 30 Super kit (Nippon Roche K.K.). The similar procedure was repeated once again for further purification to obtain 34.5 µg of highly purified poly(A)⁺ RNA from 2 mg of total RNA.

3. Preparation of a cDNA library from horseshoe crab hemocytes.

(1) Synthesis of cDNA cDNA was synthesized from poly(A)⁺RNA obtained in the above mentioned process 2.using Superscript™ Choice System (Gibco BRL Co., Ltd.).

(2) Preparation of a cDNA library

λZIPLOX horseshoe crab hemocyte cDNA library was prepared from cDNA prepared in the above mentioned process 3. (1) using a λZIPLOX, EcoR$^I$ Arms™ (Gibco BRL Co., Ltd.) and λPackaging System.

4. cDNA cloning of polypeptide.

A DNA fragment encoding for a part of polypeptide of (Formula 3] was amplified using phage DNA prepared from λgt10 cDNA library prepared by Seki, N., et al. (J. Biol. Chem., 269, 1370–1374 (1994)) as a template and two oligonucleotides as primers, synthesized in the above process 1. and a synthetic oligonucleotide having the same 3'-ATGGGACCTTCTTTATGAGTAT-5' sequence with that of around EcoR[1] restriction enzyme recognition sequence of phage vector λgt10 by PCR method (Saiki, R. K., et al. Science, 239, 487–491 (1988)). The DNA fragment was labeled with [α-$^{32}$P]dCTP using a Ready-to-Go™ DNA labeling kit (Pharmacia Biotech Co., Ltd.) to obtain a DNA probe. The probe was used for screening the λZIPLOX cDNA library prepared in the above mentioned 3.(2) to obtain a positive clone containing the longest insert cDNA having 581 bp. The nucleotide sequence of the insert a cDNA was analyzed.

5. Determination of a cDNA nucleotide sequence encoding for the polypeptide

The positive clone obtained by the above mentioned process 4. was transfected to attached E. coli DH10B(ZIP) according to the direction in the package insert of λZIPLOX, EcoR$^I$ Arm™ to give a plasmid containing cDNA encoding said polypeptide. A subcloning with deletion using a restriction enzyme recognition site on cDNA fragment and Kilo-sequence deletion kit (Takara Shuzo Co., Ltd.) was performed to determine the total nucleotide sequence of the insert cDNA. The nucleotide sequence of the cDNA of clone prepared by the above mentioned procedure was determined using a DNA sequencer 373A (Applied Biosystems Japan Co., Ltd. (ABI Co., Ltd.)). In the process, a universal primer.(ABI Co., Ltd.), synthetic oligonucleotides (5'- T G T A A A A C G A C G G C C A G T - 3 ' , 5'-CAGGAAACAGCTATGACC-3'), mimicked the nucleotide sequence of M13 reverse primer and a synthetic oligonucleotide (5'-CGAGCCTCTTCTGATAAC-3') prepared by reverse translation of Arg-Ala-Ser-Ser-Asp-Asn sequence in the amino acid sequence of polypeptide of [Formula 3] were used as sequencing primers, since the plasmid containing insert cDNA obtained from positive clone was an M13 plasmid.

The determined nucleotide sequence of the cDNA of said polypeptide and the deduced amino acid sequence are shown in Sequence table, Seq. No. 5. The determined amino acid sequence includes the complete amino acid sequence (Seq. No. 1) determined by Example 2, and the insert cDNA whose nucleotide sequence was determined by the procedure, was determined to encode the polypeptide of the present invention.

[EXAMPLE 8]

(Preparation of a pharmaceutical composition)

(1) External preparation for wound healing:

| 1 g cream | |
|---|---|
| Polypeptide obtained by Example 1 | 10 mg |
| Sorbitan monostearate | 7 mg |
| Polyoxyethylene sorbitan monostearate | 7 mg |
| Isopropyl palmitate | 37 mg |
| Vaseline | 37 mg |
| Liquid paraffin | 37 mg |
| Cetanol | 50 mg |
| Glycerin | 70 mg |
| Magnesium stearate | 2 mg | were added to purified water to make 1 g cream (2) Oral preparation

| A polypeptide fraction of Example 5 | 100 mg |
|---|---|
| Lactose | 80 mg |
| Total | 180 mg |

Above components were homogeneously mixed and placed into a hard capsule to give a capsule preparation.

We claim:

1. An isolated polypeptide consisting of the following amino acid sequence shown by Formula 1 (SEQ ID NO: 7):

```
AA1 AA2 Cys  AA2 AA2 AA2 AA1 AA2 AA4 Cys  Arg Ser AA1 Cys Phe
           5                    10                       15

Arg AA1 Glu  AA4 AA2 AA3 AA2 AA4 AA4 Ser  Ala AA2 Cys Gly Arg
            20                   25                       30

Tyr AA4 Cys  Cys Arg AA2 AA1    Formula 1    (SEQ ID NO: 7)
            35
``` wherein AA1 represents a basic amino acid residue, AA2 represents a neutral amino acid residue, AA3 represents an acidic amino acid residue, and AA4 represents an aromatic amino acid residue, respectively.

2. The polypeptide according to claim 1, wherein AA1 represents a basic L-amino acid residue selected from the group composed of Arg, Lys and His, AA2 represents a neutral L-amino acid residue selected from the group composed of Gly, Ala, Leu, Val, Ile, Met, Pro, Asn, Thr, Ser and Gln, AA3 represents an acidic L-amino acid residue selected from the group composed of Asp and Glu, and AA4 represents an aromatic L-amino acid residue selected from the group composed of Trp, Tyr and Phe in (SEQ ID NO: 7).

3. An isolated polypeptide consisting of the following amino acid sequence shown by Formula 2 (SEQ ID NO: 2):

```
                                                    Formula 2
His Ser Cys Ala Gly Asn Arg Gly Trp Cys Arg Ser Lys Cys Phe
           5                    10                       15

Arg His Glu Tyr Val Asp Thr Tyr Tyr Ser Ala Val Cys Gly Arg
            20                   25                       30

Tyr Phe Cys Cys Arg Ser Arg (SEQ ID NO:2)
            35
``` wherein the cysteine residues at the 3rd, 10th, 14th, 28th, 33rd and 34th positions may form a disulfide bond (—S—S—) between at least one combination of 3rd and 34th, 10th and 28th, and 14th and 33rd positions.

4. An isolated polypeptide consisting of a primary structure of amino acid sequence shown by Formula 4 (SEQ ID NO: 3):

```
                                                    Formula 4
Ala Ser Ser Asp Asn His Ser Cys Ala Gly Asn Arg Gly Trp Cys
1                    5                    10                       15

Arg Ser Lys Cys Phe Arg His Glu Tyr Val Asp Thr Tyr Tyr Ser
                    20                   25                       30

Ala Val Cys Gly Arg Tyr Phe Cys Cys Arg Ser Arg (SEQ ID NO:3)
                    35                   40
``` wherein one Arg may be bound through peptide linkage to the amino terminal and cysteine residues at 8th, 15th, 19th, 33rd, 38th and 39the positions may form a disulfide bond (—S—S—) between at least one combination of 8th and 39th, 15th and 33rd, and 19th and 38th positions.

5. A method for treating a living body infected by Gram-negative bacteria comprising administering to a living body in need of such treatment a therapeutically effective dosage of a polypeptide having an amino acid sequence shown by Formula 4 (SEQ ID NO: 3) or a pharmacologically acceptable salt thereof.

6. A method for treating a living body infected by Gram-positive bacteria which comprises administering to a living body in need of such treatment a therapeutically effective dosage of a polypeptide having an amino acid sequence shown by Formula 5 (SEQ ID NO: 4) or a pharmacologically acceptable salt thereof:

```
                                                    Formula 5
Asn Pro Leu Ile Pro Ala Ile Tyr Ile Gly Ala Thr Val Gly Pro
1                5                   10                       15

Ser Val Trp Ala Tyr Leu Val Ala Leu Val Gly Ala Ala Ala Val
                    20                   25                       30

Thr Ala Ala Asn Ile Arg (SEQ ID NO:4)
                    35
```

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear     ( i x ) FEATURE:
        ( A ) NAME/KEY: Peptide
        ( B ) LOCATION: 1..79
        ( D ) OTHER INFORMATION: /label=FORMULA 3

( x i ) SEQUENCE DESCRIPTION: SEQ ID NO:1:

```
Asn Pro Leu Ile Pro Ala Ile Tyr Ile Gly Ala Thr Val Gly Pro Ser
 1               5                  10                  15
Val Trp Ala Tyr Leu Val Ala Leu Val Gly Ala Ala Ala Val Thr Ala
            20                  25                  30
Ala Asn Ile Arg Arg Ala Ser Ser Asp Asn His Ser Cys Ala Gly Asn
        35                  40                  45
Arg Gly Trp Cys Arg Ser Lys Cys Phe Arg His Glu Tyr Val Asp Thr
    50                  55                  60
Tyr Tyr Ser Ala Val Cys Gly Arg Tyr Phe Cys Cys Arg Ser Arg
65                  70                  75
```

( 2 ) INFORMATION FOR SEQ ID NO:2:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear     ( i x ) FEATURE:
        ( A ) NAME/KEY: Peptide
        ( B ) LOCATION: 1..7
        ( D ) OTHER INFORMATION: /label=FORMULA 2

( x i ) SEQUENCE DESCRIPTION: SEQ ID NO:2:

```
His Ser Cys Ala Gly Asn Arg Gly Trp Cys Arg Ser Lys Cys Phe Arg
 1               5                  10                  15
His Glu Tyr Val Asp Thr Tyr Tyr Ser Ala Val Cys Gly Arg Tyr Phe
            20                  25                  30
Cys Cys Arg Ser Arg
        35
```

( 2 ) INFORMATION FOR SEQ ID NO:3:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear     ( i x ) FEATURE:
        ( A ) NAME/KEY: Peptide
        ( B ) LOCATION: 1..42
        ( D ) OTHER INFORMATION: /label=FORMULA 4

( x i ) SEQUENCE DESCRIPTION: SEQ ID NO:3:

```
Ala Ser Ser Asp Asn His Ser Cys Ala Gly Asn Arg Gly Trp Cys Arg
```

|   | 1 |   |   |   | 5 |   |   |   |   | 10 |   |   |   |   | 15 |
|---|---|---|---|---|---|---|---|---|---|----|---|---|---|---|----|
| Ser | Lys | Cys | Phe | Arg | His | Glu | Tyr | Val | Asp | Thr | Tyr | Tyr | Ser | Ala | Val |
|   |   |   |   | 20 |   |   |   |   | 25 |   |   |   |   | 30 |   |
| Cys | Gly | Arg | Tyr | Phe | Cys | Cys | Arg | Ser | Arg |   |   |   |   |   |   |
|   |   |   | 35 |   |   |   | 40 |   |   |   |   |   |   |   |   |

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear     (ix) FEATURE:
        (A) NAME/KEY: Peptide
        (B) LOCATION: 1..36
        (D) OTHER INFORMATION: /label=FORMULA 5

(xi) SEQUENCE DESCRIPTION: SEQ ID NO:4:

| Asn | Pro | Leu | Ile | Pro | Ala | Ile | Tyr | Ile | Gly | Ala | Thr | Val | Gly | Pro | Ser |
|---|---|---|---|---|---|---|---|---|---|---|---|---|---|---|---|
| 1 |   |   |   | 5 |   |   |   |   | 10 |   |   |   |   | 15 |   |
| Val | Trp | Ala | Tyr | Leu | Val | Ala | Leu | Val | Gly | Ala | Ala | Ala | Val | Thr | Ala |
|   |   |   | 20 |   |   |   |   | 25 |   |   |   |   | 30 |   |   |
| Ala | Asn | Ile | Arg |   |   |   |   |   |   |   |   |   |   |   |   |
|   |   |   | 35 |   |   |   |   |   |   |   |   |   |   |   |   |

(2) INFORMATION FOR SEQ ID NO:5:

(i) SEQUENCE CHARACTERISTICS:
        (A) LENGTH: 581 base pairs
        (B) TYPE: nucleic acid
        (C) STRANDEDNESS: single
        (D) TOPOLOGY: linear     (ix) FEATURE:
        (A) NAME/KEY: CDS
        (B) LOCATION: 21..371

(xi) SEQUENCE DESCRIPTION: SEQ ID NO:5:

```
GATTGGTATC AACAAACACA ATG AAA GGA AAC ATC GGT ATT GCT GTG TTC                50
                      Met Lys Gly Asn Ile Gly Ile Ala Val Phe
                       1               5                  10

TAC ATG TTG TTA CTT CTA CTT CCA ACA GAC AGT ATT GGG AAG AAG ATG              98
Tyr Met Leu Leu Leu Leu Leu Pro Thr Asp Ser Ile Gly Lys Lys Met
             15                  20                  25

GAA GAA GAG CAA GAG AAA CTT TTC AGA CAA AAA CGA AAT CCT CTC ATT             146
Glu Glu Glu Gln Glu Lys Leu Phe Arg Gln Lys Arg Asn Pro Leu Ile
             30                  35                  40

CCA GCA ATT TAC ATT GGA GCA ACT GTT GGG CCT TCA GTT TGG GCT TAT             194
Pro Ala Ile Tyr Ile Gly Ala Thr Val Gly Pro Ser Val Trp Ala Tyr
             45                  50                  55

CTG GTC GCT TTA GTT GGT GCC GCT GCC GTT ACT GCT GCA AAT ATA AGA             242
Leu Val Ala Leu Val Gly Ala Ala Ala Val Thr Ala Ala Asn Ile Arg
         60                  65                  70

CGA GCC TCT TCT GAT AAC CAT TCC TGT GCT GGC AAC AGA GGT TGG TGT             290
Arg Ala Ser Ser Asp Asn His Ser Cys Ala Gly Asn Arg Gly Trp Cys
 75                  80                  85                  90

AGG TCA AAG TGT TTC CGT CAC GAA TAT GTG GAC ACT TAC TAC AGT GCT             338
Arg Ser Lys Cys Phe Arg His Glu Tyr Val Asp Thr Tyr Tyr Ser Ala
                 95                  100                 105

GTA TGT GGA AGA TAC TTT TGC TGC AGA TCA CGC TAACAGATGG CACTCTGACA           391
Val Cys Gly Arg Tyr Phe Cys Cys Arg Ser Arg
             110                 115
```

| AAGTATCTGA | ATTTGAGGTG | TAACCAAGAA | AACTAAAGCC | ATATTAAGTA | AACAGTTCTA | 451 |
| AACATTTCAA | GGTATTTAGA | GTAATTTAGT | AATGTCTAGA | TAGTATTATG | TCTTCTTACC | 511 |
| AATATATATA | TTCGTAGTGT | ATGAGTATGT | TTTACGTTAT | CTGACAGTCA | ATAAATATGT | 571 |
| TTCTATCAAT | | | | | | 581 |

( 2 ) INFORMATION FOR SEQ ID NO:6:

( i ) SEQUENCE CHARACTERISTICS:
        ( A ) LENGTH: 117 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:6:

```
Met  Lys  Gly  Asn  Ile  Gly  Ile  Ala  Val  Phe  Tyr  Met  Leu  Leu  Leu  Leu
 1                   5                        10                       15

Leu  Pro  Thr  Asp  Ser  Ile  Gly  Lys  Lys  Met  Glu  Glu  Glu  Gln  Glu  Lys
                20                       25                        30

Leu  Phe  Arg  Gln  Lys  Arg  Asn  Pro  Leu  Ile  Pro  Ala  Ile  Tyr  Ile  Gly
               35                        40                   45

Ala  Thr  Val  Gly  Pro  Ser  Val  Trp  Ala  Tyr  Leu  Val  Ala  Leu  Val  Gly
          50                        55                   60

Ala  Ala  Ala  Val  Thr  Ala  Ala  Asn  Ile  Arg  Arg  Ala  Ser  Ser  Asp  Asn
 65                        70                   75                        80

His  Ser  Cys  Ala  Gly  Asn  Arg  Gly  Trp  Cys  Arg  Ser  Lys  Cys  Phe  Arg
                    85                        90                        95

His  Glu  Tyr  Val  Asp  Thr  Tyr  Tyr  Ser  Ala  Val  Cys  Gly  Arg  Tyr  Phe
                100                       105                      110

Cys  Cys  Arg  Ser  Arg
              115
```

( 2 ) INFORMATION FOR SEQ ID NO:7:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear     ( i x ) FEATURE:
        ( A ) NAME/KEY: Peptide
        ( B ) LOCATION: 1..37
        ( D ) OTHER INFORMATION: /label=FORMULA 1
            / note= "wherein each Xaa is independently selected from
            a group of one or more specified amino-acids as defined
            in the specification"

( x i ) SEQUENCE DESCRIPTION: SEQ ID NO:7:

```
Xaa  Xaa  Cys  Xaa  Xaa  Xaa  Xaa  Xaa  Xaa  Cys  Arg  Ser  Xaa  Cys  Phe  Arg
 1                   5                        10                       15

Xaa  Glu  Xaa  Xaa  Xaa  Xaa  Xaa  Xaa  Ser  Ala  Xaa  Cys  Gly  Arg  Tyr  Xaa
                20                       25                        30

Cys  Cys  Arg  Xaa  Xaa
              35
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i x ) FEATURE:
    ( A ) NAME/KEY: Peptide
    ( B ) LOCATION: 1..37
    ( D ) OTHER INFORMATION: /label=FORMULA 6

( x i ) SEQUENCE DESCRIPTION: SEQ ID NO:8:

```
His  Ser  Cys  Ala  Gly  Asn  Arg  Gly  Trp  Cys  Arg  Ser  Lys  Cys  Phe  Arg
 1              5                        10                       15
His  Glu  Tyr  Val  Asp  Thr  Tyr  Tyr  Ser  Ala  Val  Cys  Gly  Arg  Tyr  Phe
              20                       25                       30
Cys  Cys  Arg  Ser  Arg
              35
```

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

AGGAATTCGT RTCNACRTAY TCRTG                                                25

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

TATGAGTATT TCTTCCAGGG TA                                                 22

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

TGTAAAACGA CGGCCAGT                                                          18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

CAGGAAACAG CTATGACC                                                          18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CGAGCCTCTT CTGATAAC                                                                                                                          1 8